United States Patent [19]

Tucker et al.

[11] Patent Number: 5,102,797
[45] Date of Patent: Apr. 7, 1992

[54] INTRODUCTION OF HETEROLOGOUS GENES INTO BACTERIA USING TRANSPOSON FLANKED EXPRESSION CASSETTE AND A BINARY VECTOR SYSTEM

[75] Inventors: William T. Tucker; Neal I. Gutterson, both of Oakland, Calif.

[73] Assignee: DNA Plant Technology Corporation, Oakland, Calif.

[21] Appl. No.: 357,492

[22] Filed: May 26, 1989

[51] Int. Cl.$^5$ .................... C12N 15/63; C12N 15/90
[52] U.S. Cl. .......................... 435/172.3; 435/320.1
[58] Field of Search .................. 435/172.3, 320.1; 935/24, 79

[56] References Cited

U.S. PATENT DOCUMENTS 4,940,838  4/1990  Schilperoort et al. ............ 800/205

OTHER PUBLICATIONS

Mol. Gen. Genet 213:332-338, 1988, Elliott and Roth, Characterization of Tn 10d-Cam: A Transposition-Defective Tn10 Specifying Chloramphenical Resistance.
Gene 51:91-96, 1987, Obukowicz et al., ISSOL as a Non-Self Transposable Vector Used to Integrate the Bacillus thuringiensis delta-encotoxin gene into . . . .
Biotechnology 4:446-449, May 1986, Bart et al., Permanent Insertion of Foreign Genes into the Chromosomes of Soil Bacteria.

Primary Examiner—David L. Lacey
Assistant Examiner—John D. Ulm
Attorney, Agent, or Firm—Townsend and Townsend

[57] ABSTRACT

This invention relates to a new method for inserting heterologous genes into the genome of a bacteria using a combined plasmid. The combined plasmid provides a cis complementation of transposase genes and transposable elements. The method involves the homologous recombination of a carrier plasmid and a functions plasmid to form the combined plasmid. The carrier plasmid contains a transposable element which flanks a generic expression cassette. The functions plasmid comprises transposase genes which complement the transposable element on the carrier plasmid. The combined plasmid is then transferred to a recipient and the recipient is monitored for integration of the generic expression cassette into the genome. The combined plasmid is preferably created by an in vivo homologous recombination of the carrier and functions plasmids.

17 Claims, 5 Drawing Sheets (1 OF 2)

INTRODUCTION OF HETEROLOGOUS GENES INTO BACTERIA USING TRANSPOSON FLANKED EXPRESSION CASSETTE AND A BINARY VECTOR SYSTEM

BACKGROUND OF THE INVENTION

This invention relates to a new method for inserting heterologous genes into the genome of a bacteria using a combined plasmid. The combined plasmid provides a cis complementation of transposase genes and transposable elements. The method involves the homologous recombination of a carrier plasmid and a functions plasmid to form the combined plasmid. The carrier plasmid contains a transposable element which flanks a generic expression cassette. The functions plasmid comprises transposase genes which complement the transposable element on the carrier plasmid. The combined plasmid is then transferred to a recipient and the recipient is monitored for integration of the generic expression cassette into the genome. The combined plasmid is preferably created by an in vivo homologous recombination of the carrier and functions plasmids.

INFORMATION DISCLOSURE

The use of transposons for the stable insertion of cloned DNA sequences is known. Grinter, N.J., 1983, a broad-host range cloning vector transposable to various replicons, Gene, 21:133-143. Grinter describes a dual vector system where the recipient bacterium receives from the donor bacterium both a carrier and a functions (helper) plasmid. See also U.S. Pat. No(s). 4,590,162 and 4,784,956. Modification and improvements relating to the dual plasmid system are discussed in Barry, G. F., 1986, Permanent insertion of foreign genes into the chromosomes of soil bacteria. Bio/Technology, 4:446-449.

The endotoxin from Bacillus thuringiensis has been introduced into an intact transposon Tn5 and subsequently integrated into *Pseudomonas fluorescens* and *Agrobacterium radiobacter.* Obukowicz, M. G. et al., 1986, Integration of the delta-endotoxin gene of *Bacillus thuringiensis* into the chromosome of root-colonizing strains of pseudomonads using Tn5, Gene, 45:327-331. The endotoxin was also stably integrated into a bacterial genome using a defective transposon flanking sequences complemented by a recipient cell containing the transposase regions within its chromosome.

A mono-vector system where the transposase is in cis complementation with the integrating element was described in Obukowicz, M. G. et al., 1987, IS50L as a non-self transposable vector used to integrate the Bacillus thuringiensis delta-endotoxin gene into the chromosome of root-colonizing pseudomonads, Gene 51:91-96. See also, Barry, G. F., 1988, A broad-host-range shuttle system for gene insertion into the chromosomes of Gram-negative bacteria, Gene, 71:75-84. None of the mono-vector systems described in the cited art suggest the use of a homologous recombination to construct the final transfer vector, herein described as a combined plasmid.

SUMMARY OF THE INVENTION

This invention provides for a method for the insertion of DNA into the genome of a recipient bacterium following introduction of a combined plasmid comprising a transposable cassette and a transposase gene(s) competent to transfer the cassette. The method includes the step of: recombining the carrier and functions plasmids to form the combined plasmid. The use of overlapping fragments of a selectable marker which is functional upon recombination is preferred, but any pair of homologous DNA sequences can be used as sites of recombination. Preferred selectable markers include those from the group comprising:beta-lactamases, acetyl transferases, and phosphotransferases.

Preferred transposable elements are those in which it is possible to activate transposition of derivatives of the element containing only the terminal DNA sequences by the corresponding transposase gene located elsewhere in the cell. They include those selected from the group comprising: Tn5, Tn7, Tn9, IS1, IS50 and Tn916.

The method can be used where the recipient bacteria are either gram positive or gram negative. The preferred recipient bacteria are from genera of the families Enterobacteriaceae (e.g., *E. coli,* Salmonella), Pseudomonadaceae (e.g., Psu. domonas, Xanthomonas), Rhizobiaceae (e.g., Rhizobium, Agrobacterium), and Bacillaceae (e.g., Bacillus).

The preferred transposable cassette will be a generic cassette flanked on both sides by transcription terminators, translation terminators, or combinations of both.

The preferred method for the introduction of the combined plasmid into the recipient organism is conjugation. Conjugation can be either a bi-parental mating or a tri-parental mating. The preferred helper strains for tri-parental matings are strains carrying the plasmid pRK2013 or an equivalent derivative.

The replicons of the carrier plasmid preferably provide a broad host range. By broad host range, it is meant that the replicon has a host range of at least two genera of bacteria. It is preferred that the replicon be unstable in the recipient or be a conditional mutant such that the plasmid replication can be controlled by environmental conditions, e.g., temperature or choice of growth media. The replicon of the functions plasmid is preferably non-functional in the recipient host bacterium.

More particularly the disclosed method comprises the steps of:
a. constructing a functions vector containing a transposase encoding sequence and sequence for recombinational co-integration;
b. constructing a carrier vector containing a transposable cassette which is complemented by the transposase gene sequence present on the functions vector, and sequence for recombinational co-integration with the functions vector;
c. introducing the carrier and functions plasmids into an intermediate bacterial cell;
d. selecting an in vivo recombinant displaying the activity of the selectable marker; and
e. introducing of the plasmid created in step d. to the recipient bacterium.

This invention also provides for a system for the insertion of foreign DNA into the genome of a recipient bacterium wherein the recipient receives a combined plasmid, said system comprising:
a. a functions plasmid containing a transposase encoding sequence and sequence to allow recombinational cointegration of the carrier plasmid; and
b. a carrier plasmid containing a transposable cassette which is complemented by the transposase gene(s) carried on the functions plasmid and sequence to allow the recombinational co-integration with the functions plasmid.

DETAILED DESCRIPTION

Figure 1:
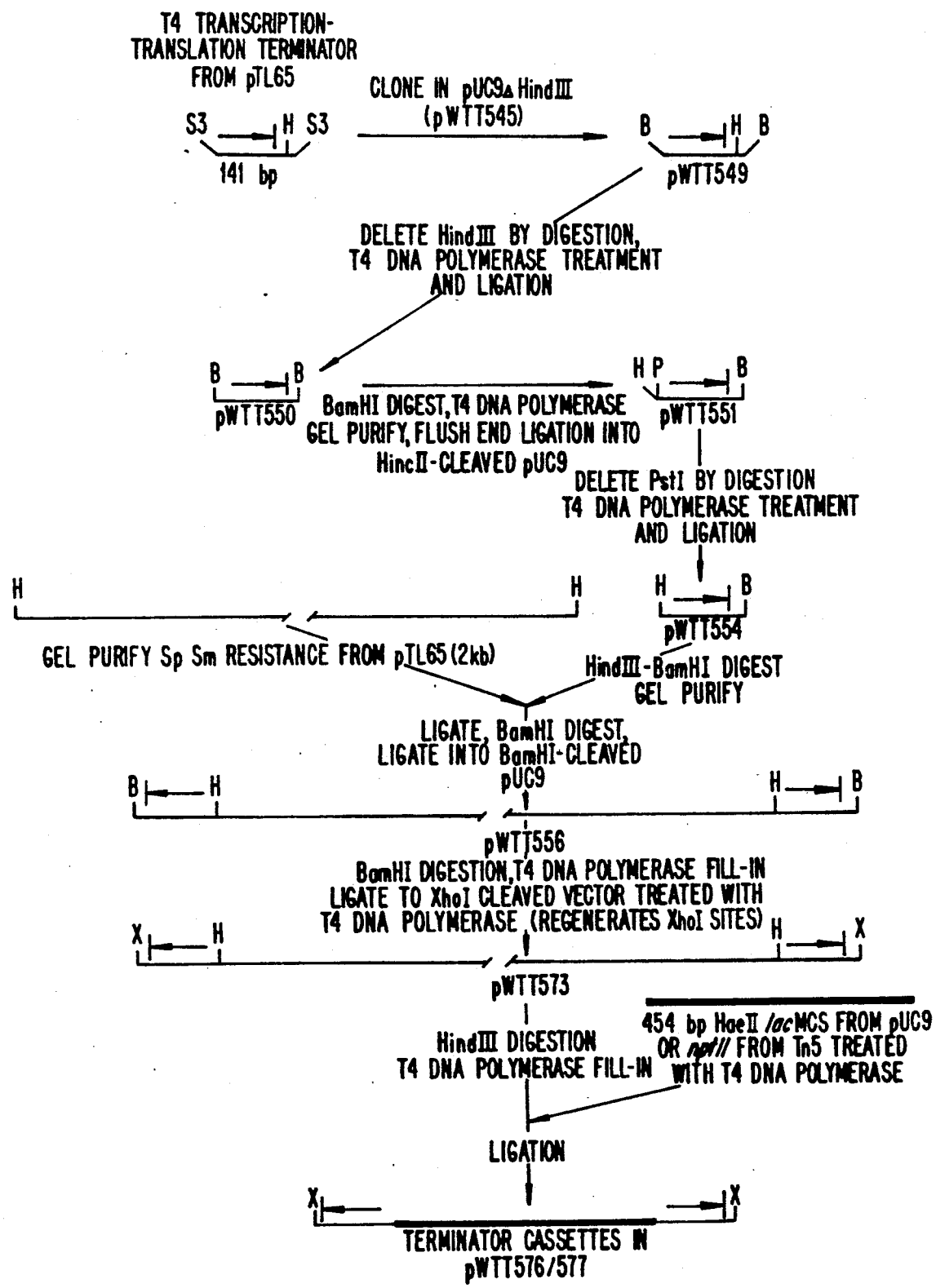
FIG. 1 is a construction of the transferable Tn7 cassette.
Figure 1:
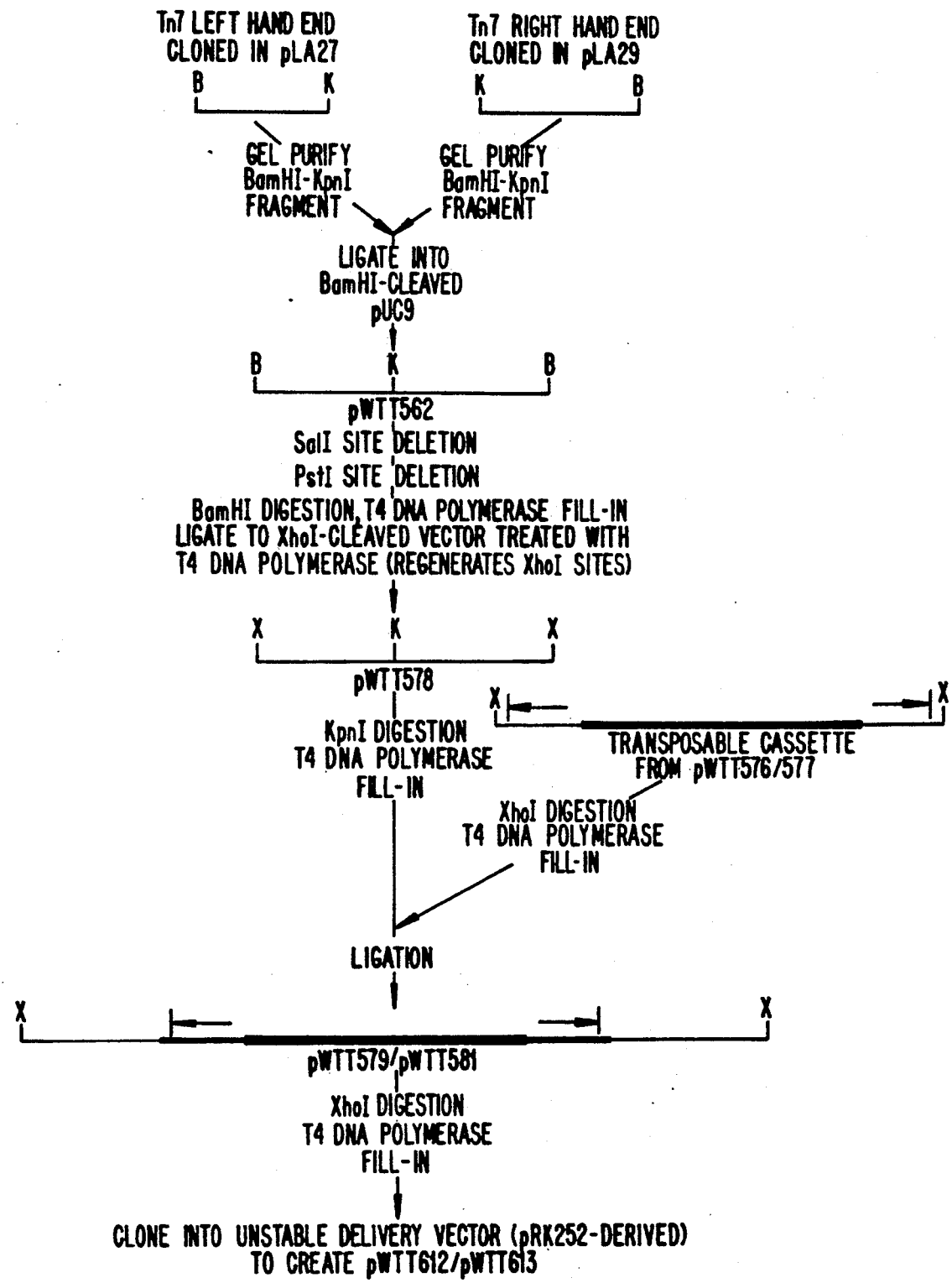

The insertion of foreign DNA into the genome of bacteria by transposition using a plasmid vector created by homologous recombination has distinct advantages over the presently available methods. The use of homologous regions to recombine the carrier and functions plasmids provides a versatility that was previously not available. One can now recombine virtually any carrier and functions plasmid without regard to either specific transposons or the presence or absence of unique restriction sites. In a preferred embodiment, the reconstruction of a selectable marker through the homologous recombination provides the additional advantage of being able to monitor the desired recombination and to maintain and select for the combined plasmid. The following disclosure will permit those of skill to appreciate the invention in its basic concept. A detailed example follows.

1. Basic Methods For Constructing the Recombinant Plasmids

Generally, the definitions of nomenclature and descriptions of general laboratory procedures used in this application can be found in Maniatis, T. et al., Molecular Cloning, A Laboratory Manual, Cold Spring Harbor Laboratory, Cold Spring Harbor, New York, 1982. The manual is hereinafter referred to as Maniatis.

All enzymes are used according to the manufacturer's instructions. Colony hybridization is carried out as generally described in Grunstein, M. et al., Proc. Nat. Acad. Sci., 72, vol. 72, pp. 3961-5 (1975).

Hybridization conditions using nick translated DNA fragments as probes are as previously described by Rigby et al., Labeling deoxyribonucleic acid to high specific activity in vitro by nick translation with DNA polymerase I, J. Mol. Biol., 113:239-251 (1977).

After hybridization, the probe containing solution is removed and saved and the filters are washed in 0.1% SDS, 2×SSC for a total of 1-2 hours with several changes of 2×SSC, 0.1% SDS. Filters are thoroughly air dried, mounted, and autoradiographed using Kodak X-OMAT AR film and Dupont Cronex Lightning Plus intensifying screens for 5-16 hours at −70° C.

Nucleotide sizes are given in either kilobases (kb) or basepairs (bp). These are estimates derived from agarose gel electrophoresis or from published DNA sequences.

Oligonucleotides that are not commercially available can be chemically synthesized according to the solid phase phosphoramidite triester method first described by Beaucage S. L. and Caruthers, M. H. Tetrahedron Letts. 22(20):1859-1862 (1981) using an automated synthesizer, as described in Needham-VanDevanter, D. R., et al., Nucleic Acids Res., 12:6159-6168 (1984). Purification of oligonucleotides is by either native acrylamide gel electrophoresis or by anion-exchange HPLC as described in Pearson, J. D. and Regnier, F. E., J. Chrom., 255:137-149 (1983).

This invention relates to cloning of intermediate vectors in prokaryotes of which genera Escherichia, Bacillus and Streptomyces are preferred. Cloning for amplification of intermediate vectors is most preferred in *E. coli* because that organism is easy to culture and more fully understood than other species of prokaryotes. The Maniatis manual contains methodology sufficient to conduct all subsequently described clonings in *E. coli*. Strain HB101 is preferred unless otherwise stated. All *E. coli* strains are grown on Luria broth (LB) with glucose, Difco's Antibiotic Medium #2 and M9 medium supplemented with glucose and acid-hydrolyzed casein amino acids. Strains with resistance to antibiotics are maintained at the drug concentrations described in Maniatis. Transformations are performed according to the method described by Morrison, D. A. (1977), J. Bacteriol., 132:349-351; or by Clark-Curtiss, J. E. and Curtiss, R., 1983, in Methods in Enzymology, 101:347-362, Wu, R., Grossman, L. and Moldave, K., eds., Academic Press, New York. Representative vectors include pBR322 and the pUC series which are available from commercial sources.

Cloning in Streptomyces has been successfully described in numerous journal articles. The book, Genetic Manipulation of Streptomyces, a Laboratory Manual, Hopwood, D. A. et al., the John Innes Foundation, Norwich, England (1985) describes in detail procedures for culturing, transformation and DNA isolation using Streptomyces as a host organism. The preferred species is *S. lividans* and frequently used cloning plasmids include pIJ61 (Gene, 20:51-62, (1982), pIJ922 (Gene 35:223-226, 1985) and pIJ702 (J. Gen. Microbiol. 129:2703-2714, 1983).

Bacillus is the third of the genera of prokaryotes preferred in this invention as cloning vectors. *Bacillus subtilis* is the best understood of the genus and is the preferred species for cloning. European patent application 146,901 offers a procedure for cloning promoters in *B. subtilis*. Culturing, transformation and DNA isolation techniques are also disclosed therein. U.S. Pat. No. 4,469,791 relating to the expression of amylolytic enzymes in Bacillus is a useful reference for teaching methods of cloning recombinant plasmids in Bacillus sps.

In order to select the transformed bacteria, selectable markers must be incorporated into the cloning vectors. These markers permit the selection of bacterial colonies containing the vectors which one desires to replicate. Examples of selectable markers include for *E. coli*: genes specifying resistance to antibiotics, i.e., ampicillin, tetracycline, kanamycin, erythromycin, or genes conferring other types of selectable enzymatic activities such as beta-galactosidase, or the lactose operon; for *Bacillus subtilis*: the neomycin resistance gene from staphylococcal plasmid pUB110 and the chloramphenicol acetyltransferase gene from staphylococcal pC194; for Streptomyces sp.: the aminoglycoside phosphotransferase (APH) gene encoding resistance to neomycin and kanamycin, the thiostrepton resistance gene, the hygromycin resistance gene, the viomycin resistance gene (see generally, Genetic Manipulation of Streptomyces, A Laboratory Manual, Ed. David Hopwood, Cold Spring harbor Laboratories, Cold Spring Harbor, New York). There are numerous other markers, known and unknown, which embody the above scientific principles, all of which would be useful as markers to detect those bacteria transformed with the vectors embraced by this invention.

The cloning vectors contain an origin of replication suitable for directing replication in prokaryotes. There are numerous examples of origin of replication markers in prokaryotes. E. coli replicons, which are the most closely studied, have origins of replication which are temperature dependent, high copy mutations, or those which constitutively sustain plasmid copies at only lower or moderate levels. Examples of E. coli origins of replication are ColEl ori, Rl ori R, or pSC101 ori.

2. The Functions plasmid

The functions plasmid contains, at a minimum, four elements: an intact selectable marker, a transposase gene(s), an origin of replication, and a sequence of nucleotides that are homologous with a region of the carrier plasmid. The intact selectable marker must function in the intermediate or donor host. Such markers are as described above and are typically antibiotic resistance (streptomycin resistance, kanamycin resistance, etc.) or a nutritional type marker such as beta-galactosidase.

The transposase element, which conveys the "functions" aspect of the functions plasmid, can be any prokaryote transposase element functional in the recipient host cell. Examples of prokaryote transposons are the Tn series 1-7, the ISl, IS50, and Tn916. For this invention, these transposons are not intact and have their transposable elements removed.

Generally, transposase gene functions which serve to insert transposable elements into the genome of the recipient organism are members of a class of enzymes which are termed "cisacting"; i.e., they function optimally to transpose DNA sequences located on the same molecule as the transposase gene(s) itself.

To facilitate insertion of DNA sequences, it is desirable that a carrier plasmid has a minimum number of restriction enzyme sites outside the transposable cassette. The inclusion of the transposase genes on the carrier plasmid would limit its usefulness due to introduction of additional restriction enzyme digestion sites present in the transposase gene sequence. The homologous recombination of the carrier and functions plasmid described in this invention achieves the desirable cis configuration of the transposable element and the transposase genes while allowing for the development of a carrier plasmid with convenient restriction enzyme sites for insertion of DNA sequences.

The functions plasmid should be stable in the intermediate host, and therefore the selection of an appropriate replicon is desirable. Because transposase gene-functions may non-specifically cause additional transposition of the inserted cassette, it is also desirable that the functions plasmid be non-transmissible to the recipient cell. It is also preferred that the functions plasmid be either non-functional or unstable in the recipient. Narrow host range plasmids which replicate only in the intermediate host are preferred. For example, replicons from the group including ColE1, pSC101 and p15A only replicate in E. coli and closely related bacteria. To achieve relative instability in the donor or recipient cells one can choose from strain dependent replicons or conditional replication mutants. For example any unstable broad host-range replicon of the incP, incQ or incW incompatibility group could be used. Alternatively, conditional mutants, such as temperature dependent replicons, could be used to eliminate functions plasmids from recipient cells.

Finally the functions plasmid must contain a sequence of nucleotides that are homologous to a corresponding sequence on the carrier plasmid. The minimum region is between 12 and 20 bases, but larger regions of homology between 400 and 1000 up are preferred. More preferred are homologous regions which are one part of a two part (bisected), selectable marker element. The two marker parts provide for an intact selectable marker upon homologous recombination with the carrier plasmid. After reconstruction, the new selectable marker must function at least in the intermediate host and optionally in the recipient host. The biscected marker can be any of the selectable markers cited above; it being understood that the other markers on the functions and carrier plasmids are distinguishable from the bisected marker.

The size of the functions plasmid is not critical. However it is preferably between about 5 and about 50 kilobases and more preferably between about 8 and about 20 kilobases.

2. The carrier plasmid

The carrier plasmid provides the transposable expression cassette destined for integration into the recipient host cell chromosome. At a minimum, the carrier plasmid also must contain a selectable marker, an origin of replication marker, and the region of homologous sequence that is a complement to the function plasmid.

The transposable expression cassette is a typical expression cassette with flanking transposon elements. Expression cassettes typically consist of an operator region composed of a promoter region, ribosomal binding region, initiation codon, followed by the open reading frame of a structural gene. The above components of an operon are well known and widely available. The specific elements of the cassette are not critical provided that consideration is given to compatibility with the recipient host.

Integration and subsequent expression of the expression cassette may inadvertently activate portions of the recipient cell genome that are adjacent to the actively expressed heterologous gene. To avoid undesired gene expression, in adjacent chromosomal regions after integration, transcription and translation terminators are inserted at the 5' and 3' regions of the cassette between the operon and the transposon flanking sequences.

Factor independent transcriptional terminators are known in the art. At least 20 terminators useful for termination of transcription in prokaryotes are known and originate from either phage or various species of bacteria. A list of these terminators, their origin and sequence can be readily found by those of skill in the art. See Ann. Rev. Genet. 13:319-353 (1979). Examples include terminators found at the following sites: E tryp att (Lee et al., J. Mol Biol., 121:193-217, 1978); and E his att (Frunzio et al., Proc. Natl. Acad. Sci. USA, 78:2767-2771, 1981); for a review, see V. Brendel and E. N. Trifonov, Nucleic Acids Research, 12(No. 10):4411-4427 (1984). The Trp a transcription terminator is commercially available from Pharmacia Inc., Piscataway, NJ 08854. These terminators are effective in Bacillus sp., Escherichia sp. and Streptomyces sp.

Translation terminators are also known. Referred to as stop codons, nonsense triplets such as UAG, UAA, UGA are known to signal the end of amino acid chain elongation by ribosomes. Insertion of such codons into DNA sequences, if not already present, is routine in the art.

The carrier plasmid must also contain an intact selectable marker that functions in both the donor and recipient host cells. In addition, the marker should be distinguishable from the intact marker located on the function plasmid. This permits the monitoring of the presence of carrier and function plasmids individually and in combination. The specific marker can be selected from those previously described with due consideration to practical matters such as the choice of host cell and the desire to monitor each plasmid independently.

The carrier plasmid must also contain the region of homologous bases for the desired recombinant event. It is preferred this region be a portion of the second part of a bisected marker gene. When the desired recombination takes place, the marker gene is restored to a functional status. The functioning marker now permits the selection of those plasmids carrying the desired recombinant.

The carrier plasmid must replicate in both the donor host cell and recipient cell. The selection of a particular origin of replication marker is dependent upon the choice of donor and recipient cells. Analogous to the situation with the functions plasmid, a conditional replication mutant could be used, and the growth conditions of the transconjugant varied to effect the loss of the combined plasmid after integration. Any unstable broad host-range replicon of the incP, incQ or incW incompatibility groups could be used.

As with the functions plasmid, the carrier plasmid could be self transmissible by conjugation, but it is not desirable to have self transmissible plasmids in recombinant strains.

The disclosed method permits both the carrier and the combined plasmid to be maintained by the recipient cell. This is an advantage over the currently available technologies, as it allows studies with the heterologous expression cassette prior to its insertion in the genome. Transposition of the expression cassette is in general more efficient from the combined plasmid than from the carrier plasmid alone.

The size of the carrier plasmid is not a critical feature. In combination with the functions plasmid, the total size should range from about 15 to about 40 kilobases.

3. Homologous recombination to form the combined plasmid

Homologous recombination can be achieved by in vitro or in vivo means. Such recombination is directed by recombination enzymes. These enzymes recognize stretches (at least about 12 to 20 bases) of homology between two DNA sequences and combine the homologous regions. The homologous recombination can either be between any homologous DNA sequences, catalyzed by the action of a recA-like protein or equivalent, or between specific sites for recombination mediated by a accompanying site-specific recombinase. The latter is exemplified by the integration of bacteriophage lambda into the *E. coli* chromosome as reviewed by Weisberg and Landy (1983) Site-specific recombination in phage lambda; in Lambda II eds. Hendrix, R. W. et al., CSH Publications, Cold Spring Harbor, N.Y. pp. 211-245.

Using these enzymes as purified reagents one can recombine the carrier and functions plasmid without the use of recombination proficient bacteria. The use of selected bacterial strains can be an undesirable restriction in some situations and the in vitro method can avoid this problem.

In vivo recombination is preferred and arises following the co-introduction of the carrier and functions plasmid into an intermediate host (donor). It is preferred that the plasmids are introduced into recombination proficient strains of bacteria such as *E. coli* (JM83), standard transformation protocols can be used. There are no additional requirements (e.g., special temperature or growth media) for the recombination.

The exemplified recombination described below utilized *E. coli* as the host and the bisected marker was the bla gene. In the hosts used, the frequency of non-homologous recombination events leading to the reconstruction of an active resistance gene (e.g. gene conversion) are negligible compared to the homologous recombination.

By appropriate selective medium, the dual transformation can be monitored and the subsequent in vivo recombination event selected.

4. Introduction of the Combined Plasmid and Integration

DNA can be introduced into recipient bacteria in a number of ways. These include conjugation, transformation, transduction, or the most recent development, electroporation. Transformation is the introduction of naked DNA into competent recipient cells. Competence may be either naturally or artificially induced using calcium or rubidium chloride. Electroporation uses pulses of high voltage electric current to enable uptake of DNA into cell protoplasts. In transduction, bacteriophages, encapsidate foreign DNA in place of their genome which is introduced into the recipient in a subsequent round of phage infection. All of the above means are suitable for introduction of the combined plasmid into the recipient bacterial host.

It is preferred that the combined plasmid be introduced into the recipient host by bacterial conjugation. Bacterial conjugation involves the physical transfer of genetic material between two cells. Conjugation is a natural event and can occur between different bacterial species. The cell delivering the genetic material is termed the donor or intermediate cell. The cell receiving the genetic material is the recipient cell or transconjugant. Conjugation will occur between bacteria of the same gram staining type i.e., gram negative or positive. *E. coli* is a preferred intermediate host and recipient host. The example offered below discloses a conjugation between an *E. coli* intermediate and a Pseudomonas species.

Conjugation may be initiated in some species of bacteria or in some strains by helper strains which provide the necessary genes for conjugation. When three strains are combined to achieve conjugation, the conjugation is termed a tri-parental mating. The third strain which activates the conjugation process is termed a "helper." In general, any broad host range plasmid, for example, those from incompatibility groups incP,Q,W and N, can be used to create a helper plasmid. Helper, intermediate and recipient bacterial cell lines are known. For example helper plasmids can be selected from bacterial strains maintaining derivatives of the R 300B, R 678 and RPB 165 and RK 2. (See U.S. Pat. No. 4,590,162 which is incorporated herein by reference, particularly column 3 lines 22-41).

The exemplified carrier plasmid is derived from the host-range replicon RK2, specifically the plasmid pRK252 (Ditta et al., 1985, Plasmid 13:149-153). It is mobilizable by the helper plasmid pRK2013 (Figurski and Helinski, 1979, PNAS 76:1648-1652) which supplies the conjugation functions lacking in pRK252. An important characteristic of this plasmid is it's instability in the recipient cell. Our derivative is very unstable in certain strains, but for reasons not well understood, the degree of instability is very much strain dependent.

The combined plasmid is mobilized by the same mechanism as the carrier plasmid. A strain harboring the helper plasmid pRK2013 is mixed with the donor and recipient cells and the mixture incubated for 4-8 hours at 28° C. During the mating, the helper plasmid (pRK2013) is transferred into the donor cell where it activates the mobilization of itself and the combined plasmid into the recipient. pRK2013 is a ColE1 (narrow host-range) replicon, non-replicative in non-enteric recipient cells.

Integration takes place as a result of the transposition of the cassette from the combined plasmid to the recipient bacteria's genome. The exemplified target is the bacterial chromosome but the invention embraces any nucleic acid which is a part of the bacterial genome including plasmids and bacteriophage nucleic acid.

Definitions:

The phrase "DNA sequence" refers to a single or double stranded deoxyribonucleic acid molecule comprised of nucleotide bases, adenosine, thymidine, cytosine and guanosine.

The term "downstream" refers to DNA sequences proceeding farther in the direction of expression; for example, the coding region is downstream from the initiation codon. Downstream is also described as the 3' region.

The phrase "expression cassette" refers to a complete unit of gene expression and regulation, including structural genes and regulating DNA sequences recognized by regulator gene products. A "transposable generic expression cassette" refers to an expression cassette having appropriate restriction sites for the insertion of different structural genes. Such genes may optionally comprise their natural control sequences. The 5' and 3' ends of the transposable generic expression cassette would comprise sequences recognized by transposases such that the entire expression cassette can be inserted into the bacterial chromosome.

The term "genome" refers to genetic makeup of a bacteria and includes the chromosome, naturally occurring plasmids, recombinant plasmids and bacteriophages.

The phrase "heterologous protein(s)" refers to proteins which are normally not produced at all by the host cell or are normally produced only in limited amounts. In general, the objective of recombining the DNA encoding the heterologous protein to a vector is to produce copious amounts of the protein.

The phrase "homologous recombination" or "recombining homologous regions" refers to the process of joining sequences of nucleic acid based on sequence homology. Typically an in vivo event, cellular enzymes recognize sequence identity between two distinct nucleic acids and effect a ligation between previously separate nucleic acids. It is distinguished from recombinations using restriction enzymes and ligases which require sequence specificity. Homologous recombination can be, but is typically not, sequence specific and requires homology of about 12 or more bases.

The term "maintained" refers to the stable presence of a plasmid within a transformed host wherein the plasmid is present as an extra-chromosomal replicating body or as an integrated portion of the host's genome.

The term "plasmid" refers to a replicating extrachromosomal circular DNA and includes both the expression and nonexpression types. "Derivatives" of plasmids refer to plasmids modified to an unspecified degree yet maintaining the salient characteristics needed to achieve a desired effect, e.g., transfer of a replicon from plasmid "a" to plasmid "b" makes plasmid "b" a derivative of plasmid "a".

The term "promoter" refers to a region of DNA involved in binding the RNA polymerase to initiate transcription.

The phrase "sequence to allow recombinational cointegration" refers to homologous sequences where homologous recombinations occur.

The phrase "structural gene" refers to DNA sequences which code for any RNA or protein product other than a regulator protein.

The phrase "transcription terminator" refers to DNA sequences that normally cause the release of the RNA polymerase from the DNA being transcribed.

The phrase "transposase encoding sequence" refers to an expressible DNA sequence encoding the transposase or transposases necessary to effect transposition of the complementary transposon elements flanking the expression cassette.

The term "upstream" refers to DNA sequences proceeding in the opposite direction from expression; for example, the bacterial promoter is upstream from the transcription unit, the initiation codon is upstream from the coding region. Upstream is also referred to as the 5' region.

The following example is merely a working embodiment of the above described invention. It should in no way be construed as a limitation or preferred embodiment of this invention.

EXAMPLES

Standard Media and Methodology

In the plasmid constructions detailed below, the following standard media were used. Bacteria were grown on LB agar (Miller, 1972, Exp. in Mol. Genetics, CHS Publications, Cold Spring Harbor, N.Y.) and supplemented with antibiotics as indicated. The antibiotics were included at the following final concentrations: ampicillin, 75 $\mu$g/ml; chloramphenicol, 50 $\mu\mu$g/ml; gentamicin, 20 $\mu$g/ml; kanamycin, 50 $\mu$g/ml; spectinomycin, 100 $\mu$g/ml; streptomycin, 100 $\mu$g/ml; tetracycline, 25 $\mu$g/ml. Plates containing the chromogenic substrate 5-bromo-4-chloro-3-indolyl-beta-D-galactoside (X-gal), and the non-metabolizable inducer isopropylthiogalactoside (IPTG; Miller, 1972, supra) were used to detect the presence of the lacZ-alpha gene fragment.

Unless explicitly stated, standard methods (Maniatis et al., 1982, supra) were used in all DNA manipulations. Restriction digests were routinely performed in TA buffer (Wartell and Reznikoff, 1980 Gene 9:307-319) or the buffer recommended by the enzyme supplier, unless otherwise stated. Ligation reactions were performed in 1×TA buffer supplemented with ATP at a final concentration of 10 mM. The screening of putative recombinant plasmids was routinely performed on small-scale preparations of plasmid DNA prepared by a modification of the method of Birnboim and Doly (Nuc. Acid Res., 7:1513-1523, 1979), as described by Maniatis et al. (1982).

I. CONSTRUCTION OF THE CARRIER PLASMID

A. Construction of the Transposable TN7 Cassette (see FIG. 1).

1. Manipulation of the T4 transcription-translation terminator

The Omega fragment containing a T4 transcription-translation terminator with a spectinomycin/streptomycin marker insert (Prentki and Krisch, 1984, Gene 29:303-319) was purchased from Amershamt and introduced into the BamHI site of the plasmid pUC18 (Yanisch-Perron, et al., 1985, Gene, 33:103-119) to create the plasmid pTL65. The T4 transcription-translation terminator was excised from pTL65 as a 141 base pair (bp) Sau3a fragment. Approximately 100 micrograms (μg) of plasmid DNA was digested to completion sequentially with Sau3a and PvuII in the buffers recommended by the enzyme supplier. The addition of PvuII to the reaction removes an interfering 141 bp Sau3a fragment from the mixture. The digested DNA fragments were separated on a preparative 10% polyacrylamide gel run in Tris-Borate-EDTA (TBE) buffer. The portion of the gel containing the appropriately sized fragment was excised and the DNA eluted into 500 μl of 0.1×TBE. The preparation was extracted once with phenol:chloroform (P:C; 1:1) and ethanol precipitated. The fragment was resuspended in 50 μl TE buffer.

To manipulate the terminator fragment, it was introduced into the plasmid pWTT545, a derivative of pUC9 (Vieira and Messing, 1982, Gene 19:259-268) in which the HindIII site in the polylinker had been removed by digestion with HindIII, treatment with T4 DNA polymerase (Wartell and Reznokoff, 1980, Gene 9:307-320), and relegation. pWTT545 DNA (5 μg) was digested to completion with BamHI, P:C extracted, precipitated, and dissolved in 25 μl TE buffer. 5 μl (approx. 1 μg) of this preparation was mixed with 2 μl of the purified T4 terminator fragment and ligated overnight at room temperature in a final volume of 10 μl.

The entire ligation mix was transformed into 100 μl competent *E. coli* HB101 (Boyer and Rolland-Dussoix, 1969, J. Mol. Biol. 41:459) cells and ampicillin resistant colonies selected. Plasmid DNA from 18 colonies was isolated and screened for the presence of a 141 bp BamHI fragment. The insertion of the correct Sau3a fragment results in the reconstruction of BamHI sites at both ends. The digested plasmid DNA samples were run on an 8% polyacrylamide gel and a plasmid with the correct structure chosen. This plasmid was given the designation pWTT549.

The HindIII site within the terminator fragment was deleted by digestion of 5 μg of pWTT549 to completion with HindIII, treatment with T4 DNA polymerase and self ligation as described above. The ligation mix was transformed into HB101. Plasmid DNA from 12 ampicillin resistant colonies were screened for the presence of a HindIII site. One HindIII site-deleted plasmid was retained as pWTT550.

The ends of the terminator fragment cloned in pWT550 were further manipulated by recloning the fragment into pUC9. 20 μg of pWTT550 DNA was digested to completion with 100 U BamHI in a final volume of 200 μl of TA buffer. The DNA preparation was then treated with T4 DNA polymerase to produce a flush ended fragments. The terminator fragment was separated from the vector sequences on an 8% polyacrylamide gel and purified by electroelution into 0.1×TBE. The sample was P:C extracted and the DNA ethanol precipitated. The purified fragment was dissolved in 25 μl TE. pUC9 DNA (5 μg) was digested to completion with HincII, P:C extracted and ethanol precipitated. The vector DNA was dissolved in 25 μl TE. 5 μl of the purified fragment and 5 μl of the cleaved vector DNA were ligated together overnight at room temperature in a final volume of 20 μl. The ligation mix was transformed into competent JM109 (Yanisch-Perron et al., 1985 Gene 33:103-119) cells and transformants selected on LB plates containing 75 μg/ml ampicillin, X-gal and IPTG.

The presence of the terminator fragment in the transformants was detected by hybridization of the colonies (Grunstein and Hogness, 1975 PNAS 72:3961-3965) to a probe made by nick translation (Rigby et al., 1977 J. Mol. Biol. 113:239-251) of the purified 141 bp terminator fragment. Plasmid DNAs from 18 possible recombinants were screened by co-digestion with BamHI and HindIII. In the desired plasmid, there should be a band of 181 bp resulting from the insertion of the pWTT550 terminator into the pUC9 polylinker. Of the 18 clones selected, 12 had BamHI-HindIII fragments of the appropriate size.

To determine the orientation of the terminator relative to the restriction sites of the pUC9 polylinker in the recombinants, the 12 samples were digested with FokI. FokI cuts asymmetrically within the terminator and therefor the orientation of the fragment can be deduced by examination of the sizes of the resulting DNA fragments. On the basis of these digestions, two plasmids were selected which differed in the orientation of the cloned fragment is such that transcription in the direction HindIII to BamHI is terminated, while in pWTT552, transcription in the direction BamHI is terminated. The orientation of the terminator fragment in these plasmids was confirmed by digestions with both AluI and HphI.

The PstI site in the plasmid pWTT551 was removed by PstI digestion, T4 DNA polymerase treatment, and self ligation, as described previously. This resulted in the plasmid pWT554.

2. Assembly of the transcription-termination cassette

To assemble the cassette, the internal HindIII fragment of the Omega element (from which the terminator was isolated) was used as a "spacer" between inverted transcription-translation terminators. This is necessary to prevent the formation of a lethal palindromic element when the two terminators are cloned "head-to head".

A HindIII fragment encoding spectinomycin-streptomycin (Sm$^r$Sp$^r$) resistance was purified from 50 μg of pTL65 which had been digested to completion with 300 U HindIII. The approx. 2 kb DNA fragment was eluted from a 0.8% low melting temperature agarose gel run in TBE buffer. The DNA was P:C extracted, ethanol precipitated and the pellet dissolved in 50 μl TE.

The modified terminator fragment was purified from 20 μg of pWTT551 DNA digested to completion with BamHI and HindIII by polyacrylamide gel electrophoresis, elution and precipitation as described previously. The DNA pellet was dissolved in 25 μl of TE.

This terminator fragment (10 μl) was ligated to Sm$^r$Sp$^r$ fragment (5 μl) for 2 h at room temperature in a final volume of 20 μl. 20 U BamHI was added to the reaction and the sample incubated at 37° C. for a further 2 h. The reaction was then P:C extracted, precipitated, and dissolved in 25 µl TE. 5 µl of this DNA preparation was ligated to 1 µg of BamHI cleaved pUC9 DNA in a final volume of 20 µl. The ligation mix was transformed into competent JM109 cells and white, ampicillin resistant cells selected on LB agar containing ampicillin, X-gal and IPTG. Of 100 such colonies screened for streptomycin and spectinomycin resistance, 25 had the appropriate resistances. Plasmids from 12 of these 25 were subjected to restriction analysis with either BamHI or HindIII. All had fragment sizes consistent with the insertion of the HindIII Sm$^r$Sp$^r$ fragment between the transcription-translation terminator fragments. One of these was saved and designated pWTT556.

For the next set of manipulations a series of plasmids were created by restriction site deletions of the plasmids pACYC184 and pWTT503. pWT503 is plasmid pACYC184 (Chang and Cohen, 1974 J. Bacteriol. 134:1141–1156) from which the SalI site has been removed, and into which the HindIII-SalI fragment of transposon Tn5 (Jorgensen et al., 1979 Mol. Gen. Genet. 177:65–72) has been inserted. The plasmid encodes resistance to kanamycin and chloramphenicol. Plasmid pWTT558 is a derivative of pWTT503 from which the HindIII site was deleted in a manner analogous to that described earlier, and pWTT561 was derived from pWTT558 by removal of the SalI site in the non-coding region of the Tn5-derived sequences of pWTT503. Both pWTT558 and pWTT561 have a unique XhoI site originating from the Tn5 sequence inserted in the pACYC184 vector. pWTT569 was derived from pACYC184 by deletion of the HindIII site.

The Sm$^r$Sp$^r$-terminator cassette was first inserted into the unique XhoI site of pWTT558. To accomplish this, 5 µg of pWTT556 and pWTT558 were digested with BamHI and XhoI and subsequently treated with T4 DNA polymerase to produce flush ended fragments. 1 µg of each DNA preparation was ligated together overnight in a final volume of 20 µl. The ligation mix was transformed into HB101 and chloramphenicol resistant, spectinomycin resistant cells selected. Plasmid DNA from 12 such colonies was screened by XhoI digestion to detect the presence of a DNA fragment the same size as the BamHI fragment for pWTT566. Of the 12, 5 had the desired fragment and one was saved and designated pWTT563. The terminator cassette from pWTT563 was then moved as a BamHI-SalI fragment to BamHI-SalI digested pWTT569 to create plasmid pWTT573.

To create the final terminator cassette, the lacZ-alpha fragment from pUC9 or a combination of the lacZ-alpha and the Tn5 nptII (Jorgensen et al., 1979 supra) fragments were substituted for the Sm$^r$Sp$^r$ fragment of plasmid pWTT573. 10 µg of plasmid pWTT573 was digested with HindIII and treated with T4 DNA polymerase to create flush ends.

100 µg pUC9 was digested with HaeII and also treated with T4 DNA polymerase and the approximate 450 bp flush ended fragment encoding the lacZ-alpha polypeptide and multicloning site (lacMCS) was purified by electroelution from a 1.4% low melting point agarose gel. The DNA fragment was dissolved in a final volume of 25 µl TE.

The Tn5 nptII gene fragment was derived from the plasmid pGJ67. pGJ67 is unpublished but is analogous to pWTT503 except that rt retains the SalI site present in pACYC184). 5 µg of pGJ67 was digested with BamHI and SmaI and treated with T4 DNA polymerase. The desired fragment was eluted from a 1% low melting point agarose gel and dissolved in a final volume of 25 µl.

Introduction of the lacMCS and nptII genes into pWTT573 was achieved by ligating 5 µl of either purified lac-MCS fragment or 5 µl of the lacMCS and 5 µl of the nptII fragment with 1 µg of the HindIII-T4 DNA polymerase treated pWTT573 DNA in a final volume of 20 µl. The ligation reactions were transformed into JM109 and transformants selected on LB agar plates containing X-gal and IPTG, supplemented with chloramphenicol or kanamycin respectively.

Plasmid DNA from 12 blue chloramphenicol resistant colonies were screened by XhoI digestion for a band of approximately 700 bp. Of these, 11 had the correct structure, and one was saved as pWTT576.

Similarly, plasmid DNA from 12 blue kanamycin resistant colonies were screened and 8 of these had the correct structure. These 8 were analyzed further by BamHI-BglII restriction enzyme digestion to determine the relative orientation of the lacMCS and nptII fragments. One plasmid in which the direction of transcription of both genes was the same was saved and designated pWTT577.

3. Assembly of the transposable cassette

The left end (166 bases) and right end (199 bases) of Tn7 were cloned in the plasmids pLA27 and pLA29, respectively. Both ends were isolated as BamHI-KpnI fragments and purified from 10 µg of digested plasmid DNA by elution from 8% polyacrylamide gels. The DNA was precipitated and dissolved in 25 µl TE. 5 µl of each DNA sample was ligated together overnight in a final volume of 20 µl. The ligation mix was then digested with 20 U BamHI in a final volume of 50 µl for 1 h at 37° C. The reaction was then P:C extracted, ethanol precipitated, and the DNA pellet dissolved in 25 µl TE.

The ligated ends of Tn7 were then cloned into pUC9 yielding pWTT562. 5 µl of the preparation was ligated to 1 µg of BamHI-cleaved pUC9 overnight in a final volume of 20 µl. The ligation mix was transformed into JM109 and white, ampicillin resistant colonies selected. Plasmid DNA from 18 such colonies was screened by BamHI digestion for the presence of a DNA fragment of approximately 0.5 kb. In this experiment, "head-to-head" ligation of either two left or two right ends creates a lethal palindrome so that all fragments of the appropriate size will contain one left and one right end. Of 18 transformants screened, 9 had a fragment of the correct size, and one was saved as pWTT562. When tested, this plasmid had a single KpnI site, confirming the identity of the construction.

The ligated Tn7 ends from pWTT562 were recloned as a BamHI fragment into the plasmid pWTT561. The small fragment composed of the Tn7 ends was purified by elution from a 1% low melting point agarose gel and dissolved in a final volume of 25 µl TE. 5 µg of pWTT561 was digested with XhoI and treated with T4 DNA polymerase to create flush ends. 1 µg of this DNA preparation was ligated overnight to 10 µl of the purified Tn7 ends fragment in a final volume of 20 µl. The ligation mix was transformed into HB101 and chloramphenicol resistant colonies selected. These transformants were screened by colony hybridization to a nick translated probe made from pLA27. Plasmid DNA from 8 positively hybridizing colonies were analyzed by restriction enzyme digestion with XhoI for a DNA fragment of the same size as the small BamHI fragment of pWTT562. One plasmid with the desired structure was saved as pWTT572.

A SalI site in the Tn7 ends was removed from pWTT572 by sequential restriction enzyme digestion, T4 DNA polymerase treatment and self-ligation. This plasmid was designated pWTT574. Similarly, the kanamycin resistance of pWTT574 was eliminated by deletion of the PstI site in the nptII gene to create pWTT578.

Into pWTT578 was inserted the lacMCS or the KmlacMCS terminator cassettes from pWTT576 and pWTT577 respectively. The cassette-containing fragments from these plasmids were purified by elution from 1% low melting point agarose gels of DNA that had been cleaved with XhoI and treated with T4 DNA polymerase to create flush ends. These DNA samples were dissolved in 25 μl TE. Plasmid DNA from pWTT578 was cleaved with KpnI and also treated with T4 DNA polymerase. Approximately 1 μg of cleaved pWTT578 DNA was ligated overnight to 5 μl of either of the purified terminator cassette fragments. These ligations were transformed into JM109 and blue, chloramphenicol resistant colonies selected on chloramphenicol, X-gal and IPTG containing LB agar plates. Plasmid DNA from three colonies from the pWTT576-pWTT578 and two colonies from the pWTT577-pWTT578 ligations were screened by XhoI digestion for fragments of the size expected from the correct ligation event. The plasmid with the appropriate Tn7-lacMCS cassette was designated pWTT579, while the plasmid with the Tn7-KmlacMCS cassette was designated pWTT581.

Figure 2:
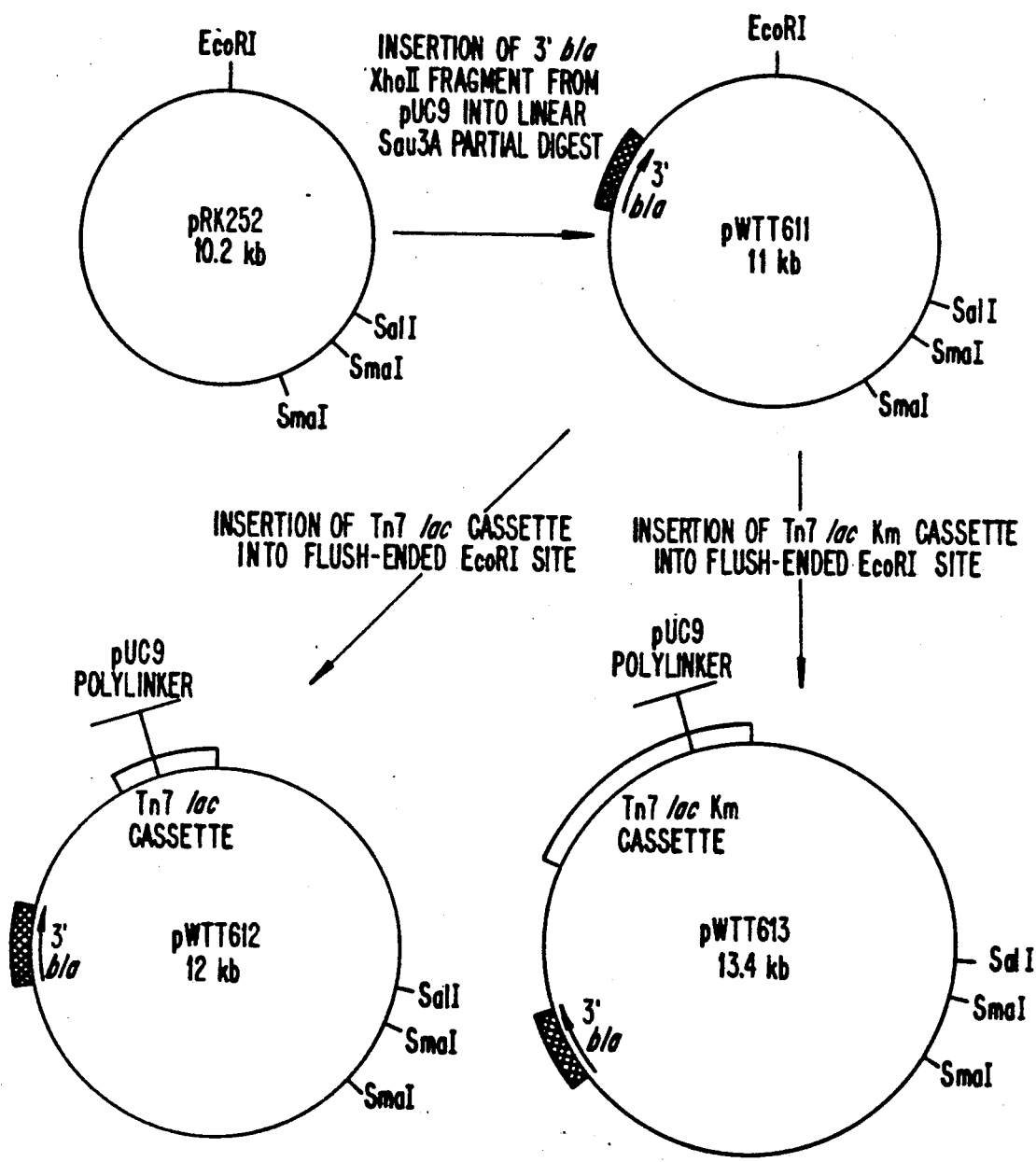
FIG. 2 is a construction of the carrier plasmid.

B. Construction of the Carrier Plasmid (see FIG. 2)

1. Insertion of the 3' beta-lactamase fragment into pRK252

The 3' bla gene segment was isolated as an XhoII fragment from the plasmid pUC9. 10 μg pUC9 was digested with ShoII and the 768/751 bp fragments purified by elution from a 1.4% low melting point agarose gel. The 3' bla fragment is 768 bp and must be separated from the 751 bp fragment with which it co-migrates. This separation was achieved by ligating the fragment mixture into BamHI cleaved pRK7813 (Jones and Gutterson, 1987 Gene 61:299-306). Insertion of fragments into the BamHI site of this vector results in white colonies when screened on tetracycline plates containing the indicator X-gal and IPTG. White colonies were screened by colony hybridization to a nick translated probe made from plasmid pCM301 (Tucker et al., 1984, Cell 38:191-201). This probe will only detect colonies which have the bla fragment. Plasmid DNA from 12 positively hybridizing clones was analyzed by BamHI digestion for the presence of a 768 bp fragment. The insertion of the desired XhoII fragment into the BamHI site of the vector results in the recreation of BamHI sites at both ends. This is not the case with the 751 bp fragment. All of the plasmids analyzed had the correct fragment pattern. One was saved and designated pWTT608.

Digestion of covalently closed circular DNA with certain restriction enzymes in the presence of limiting concentrations of ethidium bromide, results in the formation of predominately linear length molecules (Maniatis, et al., 1982 supra). The subcloned 3' bla fragment was then inserted into a linear partial Sau3a digest of the plasmid pRK252 prepared by digesting 5 μg of pRK252 DNA with 2 U Sau3a in the presence of 25 μg/ml ethidium bromide. The linear length molecules were purified by elution from a 0.8% low melting point agarose gel and dissolved in a final volume of 50 μl TE. The 3' bla fragment was purified from 10 μg of BamHI digested pWTT608 DNA by elution from a 1.2% low melting point agarose gel, and dissolved in 50 μl TE.

8 μl of the pRK252 Sau3a linear DNA preparation and 1 μl of the 3' bla fragment were ligated together in a final volume of 12 μl. This preparation was transformed into HB101 and tetracycline resistant colonies selected. These colonies were screened by colony hybridization to a pCM301 probe as described above. Plasmid DNA from 12 positively hybridizing clones was analyzed for its ability to recombine in vivo with a 5' bla fragment to create a functional bla gene.

Competent cells of JM83 (Vieira and Messing, 1982 Gene 19:259-268) were cotransformed with DNA of plasmid pWTT605 (see below) and each of the 12 putative 3' bla clones Transformants resistant to gentamicin and tetracycline were selected and a representative transformant from each plasmid combination screened on ampicillin plates for the presence of resistant colonies. Of the 12 tested, 8 gave ampicillin resistant in vivo recombinants.

Plasmid DNA from the 12 possible clones was also screened for its restriction enzyme digestion pattern with EcoRI or XhoII. Colonies whose plasmid DNA had a single EcoRI site and whose XhoII digestion pattern varied from pRK252 by only one or two bands were selected for the final screen.

To function as a carrier in the "hitch-hiker" system, the final plasmid must be able to mobilize the functions plasmid into the recipient following the in vivo recombination event. The recombinant ampicillin resistant colonies isolated earlier from the 4 plasmids which satisfied the criteria described above were tested for their ability to mobilize gentamycin resistance to the Pseudomonas fluorescens strain Hv37a (Gutterson, et al., 1986 J. Bacteriol. 165:696-703). Overnight cultures of cells harboring the putative carrier plasmids were mixed with overnight cultures of Hv37a and strain NE47 (Gutterson et al., 1986 supra) carrying the helper plasmid pRK2013 (Figurski and Helinski, 1979 PNAS 76:1648-1652). The cells were incubated o plates at 28° C. overnight and transconjugants selected on chloramphenicol, tetracycline plates. The resulting colonies were tested of their resistance to gentamicin. All four strains gave gentamicin resistant cells and the isolate which gave the highest apparent frequency of such cells while retaining the characteristic morphology of the Hv37a recipient was subjected to further restriction digestion analysis to determine the location of the insertion of the 3' bla fragment in the vector. This plasmid was given the designation pWTT611.

2. Insertion of the lacMCS and KmlacMCS cassettes into pWTT611.

The transposable cassettes created as described above were inserted into the EcoRI site of pWTT611. 5 μg of pWTT611 DNA was digested with EcoRI and treated with T4 DNA polymerase to create flush ends. pWTT579 or pWTT581 DNA was digested with XhoI and also treated with T4 DNA polymerase and the cassette-containing fragment purified by elution from 1.0% low melting point agarose gels. The DNA was dissolved in 25 μl TE. 2 μg of the cleaved pWTT611

DNA was ligated to 10 μl of either of the purified cassette fragments in a final volume of 25 μl. 10 μl of these ligation reactions were transformed into competent JM109 cells and transformants selected on tetracycline plates containing X-gal and IPTG. Plasmid DNA from 6 blue transformant colonies from each ligation mix were analyzed by restriction digestion with SmaI. All had the predicted structure. One correct plasmid from the pWTT579-pWTT611 ligation (lacMCS cassette) was designated pWTT612, and one correct plasmid from the pWTT581-pWTT611 ligation (KmlacMCS cassette) was designated pWTT613.

II. CONSTRUCTION OF THE FUNCTIONS VECTOR

A. Manipulation of the TN7 Functions

To facilitate further manipulations of the Tn7 functions region, the restriction site at one end of the fragment was altered. Plasmid DNA of pCW10 (10 μg; Waddell and Craig, 1988 Genes and Develop. 2:137-149) was digested to completion with SphI and treated with T4 DNA polymerase to create flush ends. Phosphorylated EcoRI linkers (BRL Cat No. 1013) were ligated to 1 μg of this DNA in a final volume of 10 μl. After overnight incubation at room temperature, the mixture was digested with 20 U EcoRI in a final volume of 20 μl. The digestion was then P:C extracted and precipitated and the DNA pellet dissolved in a final volume of 25 μl.

The modified functions fragment was subcloned into EcoRI cleaved pUC9. 5 μg pUC9 was digested to completion with EcoRI, and the DNA P:C extracted, precipitated, and the pellet dissolved in 25 μl TE. 5 μl of the modified functions fragment and 5 μl of the digested pUC9 plasmid were ligated together overnight in a final volume of 20 μl. The ligation mix was transformed into JM109, and white, ampicillin resistant colonies selected on Xgal and IPTG containing agar plates. Plasmid DNA from 12 such colonies was screened by EcoRI digestion for the presence of a 9 kb fragment characteristic of the Tn7 functions. One plasmid satisfying this criteria was saved and designated pWTT593.

Figure 3:
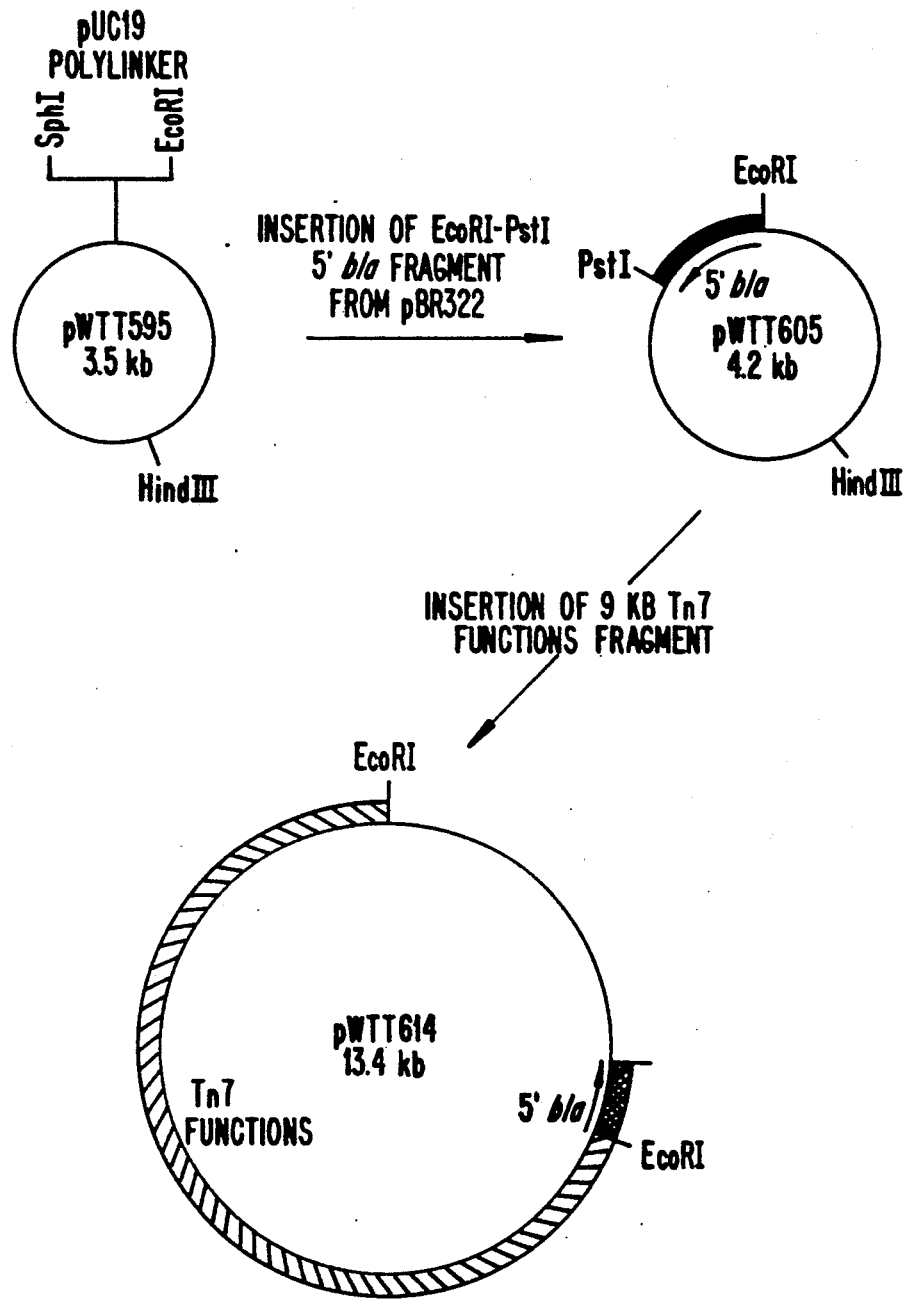
FIG. 3 is a construction of the functions plasmid.

B. Construction of the Functions Plasmid (see FIG. 3)

The narrow host range functions vector was constructed from the p15A replicon pACYC184 and the gentamycin resistance fragment from the plasmid pLVC42 (L. Corotto and G. Warren, unpublished; this plasmid has the HindIII-SphI fragment from pPHIJI (Hirsch and Beringer, 1984, Plasmid, 12:139-141) which encodes gentamycin resistance inserted into HindIII-SphI cleaved pUC19).

pACYC184 and pLVC42 DNA (5 μg each) were digested to completion with HindIII and EcoRI. The 1.75 kb pACYC184 fragment carrying the origin of replication and the 1.85 kb pLVC42 fragment encoding gentamycin resistance were purified by elution from a 1.0% low melting point agarose gel and dissolved in 25 μl TE. Approximately 1 μg of each DNA was ligated together overnight in a final volume of 20 μl. The ligation mix was transformed into competent HB101 cells and the gentamycin resistant transformants selected. A single transformant whose plasmid DNA showed the presence of only the two isolated fragments was saved as pWTT595.

Into pWTT595 was cloned the 5' bla gene fragment from pBR322. This fragment was isolated from an EcoRI-PstI digest of 5 μg of the plasmid. The approximately 0.7 kb fragment was purified by elution from a 1.4% low melting point agarose gel and dissolved in 25 μl TE. 1 μg of EcoRI and PstI cleaved pWTT595 was ligated together overnight with 5 μl of the purified 5' bla fragment in a final volume of 20 μl. The reaction was transformed into HB101 and gentamycin resistant colonies selected. These were screened by colony hybridization to a nick translated probe made from pBR322. Plasmid DNA from 12 positively hybridizing clones was analyzed for the presence of the 0.7 kb EcoRI-PstI band. One such clone was saved and designated pWTT605.

The EcoRI fragment encoding the Tn7 functions from pWTT593 was inserted into the plasmid pWTT605. 5 μg of each plasmid DNA was digested to completion with EcoRI and 1 μg of each preparation was ligated together overnight in a final volume of 25 μl. The ligation mix was transformed into JM109 and gentamycin resistant cells selected. Plasmid DNA from 12 colonies was screened by EcoRI digestion for the presence of only the two bands corresponding to the pWTT605. plasmid and the 9 kb functions fragment. Of the 12 screened, 3 had the desired structure, and one of these was saved as pWTT614.

III. INTRODUCTION OF THE KMLACMCS CASSETTE INTO THE CHROMOSOME OF P. FLUORESCENS STRAIN HV37A.

Figure 4:
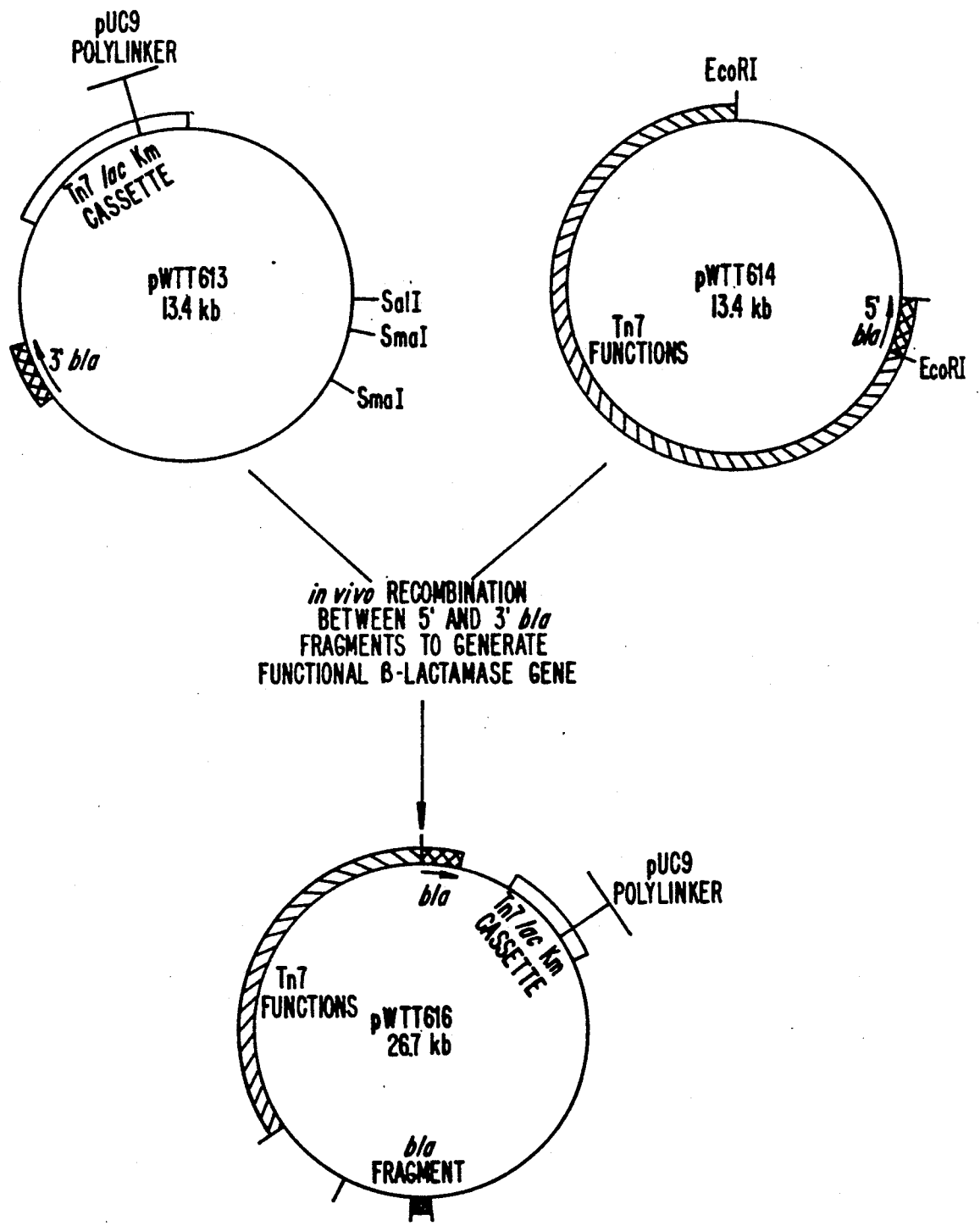
FIG. 4 is a recombination to obtain the combined plasmid.

The carrier plasmid pWTT612 and the functions plasmid pWTT614 were transformed into the recombination proficient *E. coli* strain JM83. Transformants were selected on LB plates containing tetracycline and gentamycin. A single colony from the selective plates was used to inoculate 5 ml LB broth containing both antibiotics, and grown overnight at 37° C. The culture was then diluted and plated for single colonies on LB agar containing 100 μg/ml ampicillin. Ampicillin-resistant colonies resulting from the in vivo recombination event (see FIG. 4) were detected at a frequency of $1 \times 10^{-5}$ per colony forming unit (cfu). Control experiments using a recombination deficient (Rec$^-$) *E. Coli* strain HB101 yielded Apr colonies at a frequency of $1 \times 10^{-7}$ per cfu.

*E. coli* cells containing the in vivo recombinant plasmid pWTT616 and *E. coli* strain NE47 were grown overnight at 37° C. in 5 ml LB containing tetracycline and gentamicin or kanamycin respectively. Cells of the *P. fluorescens* strain Hv37a were grown overnight at 28° C. in 5 ml LB. Cells from 1.5 ml of these cultures were pelleted by centrifugation, washed in LB and resuspended in 150 μl LB. 10 μl of each culture was mixed on the surface of an LB agar plate and incubated at 27° C. for 4-6 h. The cells were then washed off in 1 ml LB and dilutions plated on LB agar containing gentamycin, tetracycline and chloramphenicol to select Hv37a transconjugants carrying pWTT616.

Single transconjugant colonies were inoculated into 5 ml LB and grown at 28° C. in the absence of antibiotic selection for 18-24 h. The culture was then diluted and plated for single colonies on LB agar with and without kanamycin. The frequency of recovery of Km$^r$cells was $2 \times 10^{-1}$ per cfu. Kanamycin-resistant cells were then screened for their resistance or sensitivity to tetracycline and gentamycin, the antibiotic resistances determined by the vector. Transposition of the Tn7-derived cassette from the plasmid vector to the chromosome followed by loss of the recombinant carrier plasmid should yield kanamycin-resistant cells which have lost the vector-encoded resistances.

All of the 100 kanamycin resistant cells tested were sensitive to both tetracycline and gentamycin, indicating that the frequency of transposition was high. Total genomic DNA from six of the putative transposants was analyzed by southern hybridization for the presence of the Tn7-derived cassette. All carried a insertion of the cassette at the same site in the Hv37a chromosome and in the same relative orientation.

IV. INTRODUCTION OF THE P. FLUORESCENS INAW GENE INTO THE CHROMOSOME OF ICE⁻ P. FLUORESCENS STRAIN HV37A.

A 6.7 kb HindIII fragment containing the inaW gene, including its native promoter, was isolated by gel elution from a HindIII digest of the plasmid pGJ136, carrying the inaW gene. This fragment was introduced into the unique HindIII site in the lacMCS polylinker of the Tn7 carrier plasmid pWTT612. Putative recombinant colonies were identified by their white color on LB plates containing tetracycline, X-gal and IPTG. These colonies were screen for an Ice+ phenotype by tube freezing at 6° C. (Hirano, S. S., L. S. Baker and C. D. Upper. (1985) "Ice nucleation temperature of individual leaves in relation to population sizes of ice nucleation active bacteria and frost injury." Plant Physiol. 77:259-265). One Ice+, tetracycline resistant colony was saved as pWTT628.

pWTT628 DNA was cotransformed with DNA of the functions plasmid pwTT614 into the recombination proficient strain of E. coli, JM83. Tetracycline resistant, gentamycin resistant transformants were selected and a single colony inoculated into LB and grown overnight at 37° C. The culture was then plated for single colonies on LB plates containing ampicillin to select in vivo recombinants between the carrier and functions plasmid. An ampicillin resistant colony was saved as pWTT630.

P. fluorescens strain Hv37aR2 (a rifampicin resistant derivative of Hv37a) was grown overnight at 28° C. and E. coli cells carrying either pWTT630 or the helper plasmid pRK2013 (NE47) were grown overnight at 37° C. Plate matings were performed as described above (Example III) and Hv37a transconjugants carrying pWTT630 were isolated on selective media containing chloramphenicol, tetracycline and gentamycin.

Six transconjugant colonies from 3 independent matings were selected and inoculated into 5 ml LB and grown overnight in the absence of antibiotics. These cultures were plated for single colonies on LB plates and these colonies screened for their ice nucleation phenotype as described above in this Example.

Screening of these colonies resulted in Ice+ colonies being detected at a frequency of 0.04. All Ice+ colonies were sensitive to both tetracycline and gentamycin, indicating the loss of the plasmid vector sequences.

What is claimed is:

1. A method for the insertion of foreign DNA into the genome of a recipient bacterium by introduction of a combined plasmid containing a transposable cassette and a transposase encoding sequence which is competent to transpose the cassette, said method comprising the steps [step] of forming the combined plasmid from a carrier plasmid and a functions plasmid by homologous recombination wherein the recombination occurs between overlapping segments of a selectable marker such that recombination results in the construction of a functional selectable marker *followed by the introduction of the combined plasmid into the recipient bacterium.*

2. A method of claim 1 wherein the transposase encoding sequence is derived from a transposable element selected from the group consisting of Tn5, Tn7, Tn9, Tn916, IS1 and IS50.

3. A method of claim 1 wherein the selectable marker is selected from the group consisting of beta-lactamases, acetyl transferases, and phosphotransferases.

4. A method of claim 1 wherein the replicon of the carrier plasmid has a host range of at least two genera of bacterium.

5. A method of claim 1 where the replicon of the functions plasmid is non-functional in the recipient host bacterium.

6. A method of claim 1 wherein the expression cassette is flanked by transcription terminators.

7. A method of claim 1 wherein the expression cassette is further flanked by translation terminators.

8. A method of claim 1 wherein the homologous recombination occurs within a bacterial cell.

9. A method of claim 8 wherein the combined plasmid is transferred to the recipient bacterium by conjugation between a donor bacterium maintaining the combined plasmid and the recipient bacterium.

10. A method of claim 9 wherein the recipient bacterium is selected from a species in the group of families consisting of Enterobacteriaceae, Rhizobiaceae and Bacillaceae.

11. A method of claim 10 where the conjugation is a tri-parental mating.

12. A method of claim 11 wherein the tri-parental mating involves a helper strain carrying the plasmid pRK2013 or an equivalent derivative.

13. A method of claim 9 wherein the donor bacterium and recipient bacterium are both gram negative.

14. A method of claim 13 wherein the donor bacterium is *Escherichia coli.*

15. A method of claim 11 wherein the replicon is a conditional mutant.

16. A method for the insertion of foreign DNA into the chromosome of a recipient bacterium which comprises the steps of:
   a. constructing a functions vector containing a transposase encoding sequence and the first part of a 2 part selectable marker;
   b. constructing a carrier vector containing a transposable cassette which is complemented by the transposase sequence of the functions vector and the second part of a two part selectable marker wherein the second part comprises a segment which overlaps with the first part such that homologous recombination results in the construction of a functional selectable marker;
   c. transforming an intermediate bacterial cell host with the functions and carrier vectors;
   d. selecting for in vivo recombinants displaying the activity of the selectable marker; and
   e. conjugating the bacterial cells of step d with a recipient cell.

17. A system for the insertion of foreign DNA into the genome of a recipient bacterium wherein the recipient bacterium receives a combined plasmid from a donor bacterium, said system comprising:
   a. a functions plasmid containing a transposase encoding sequence selectable marker; and
   b. a carrier plasmid containing a transposable cassette which is complemented by the transposase sequence of the functions vector and a sequence of nucleotides that are homologous with a sequence of nucleotides on the functions plasmid wherein the homologous sequence of the carrier and functions plasmids are portions of an overlapping region of a bisected selectable marker that is functional upon formation of the combination plasmid by homologous recombination.

* * * * *